(12) United States Patent
Cadario et al.

(10) Patent No.: US 7,845,924 B2
(45) Date of Patent: Dec. 7, 2010

(54) SYSTEM FOR PREPARING DENTAL RESTORATIONS

(75) Inventors: Vittorio Cadario, Buchs SG (CH); Harald Bürke, Frastanz (AT); Marcel Schweiger, Chur (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 19 days.

(21) Appl. No.: 12/055,818

(22) Filed: Mar. 26, 2008

(65) Prior Publication Data
US 2009/0136901 A1 May 28, 2009

(30) Foreign Application Priority Data
Nov. 28, 2007 (EP) .................. 07023059

(51) Int. Cl.
B29C 45/13 (2006.01)
B29C 45/23 (2006.01)
A61C 13/08 (2006.01)

(52) U.S. Cl. .............. 425/130; 264/20; 425/572; 425/573; 433/203.1

(58) Field of Classification Search .......... 264/16, 264/20, 18, 19; 425/130, 573, 572; 433/203.1
See application file for complete search history.

(56) References Cited

U.S. PATENT DOCUMENTS

| | | | | |
|---|---|---|---|---|
| 3,064,309 A | * | 11/1962 | Steinbock et al. | 264/226 |
| 3,909,169 A | * | 9/1975 | Barrie | 425/130 |
| 3,947,177 A | * | 3/1976 | Eckardt | 425/130 |
| 4,189,325 A | * | 2/1980 | Barrett et al. | 106/35 |
| 4,573,842 A | * | 3/1986 | Mantela et al. | 410/23 |
| 4,573,921 A | * | 3/1986 | Berger | 433/167 |
| 4,799,887 A | * | 1/1989 | Hakamatsuka et al. | 433/212.1 |
| 5,028,226 A | * | 7/1991 | De'ath et al. | 425/130 |
| 5,702,514 A | | 12/1997 | Petticrew | |
| 6,074,190 A | * | 6/2000 | Nagaoka et al. | 425/130 |
| 6,379,593 B1 | * | 4/2002 | Datzmann et al. | 264/20 |
| 6,485,849 B2 | * | 11/2002 | Petticrew | 428/697 |
| 6,648,646 B2 | * | 11/2003 | Sato | 433/223 |
| 6,655,945 B1 | * | 12/2003 | Gellert et al. | 425/130 |
| 7,547,208 B2 | * | 6/2009 | Babin et al. | 425/562 |
| 2004/0254667 A1 | * | 12/2004 | Ganley et al. | 700/117 |
| 2005/0146064 A1 | * | 7/2005 | Fecher et al. | 264/19 |
| 2006/0151480 A1 | * | 7/2006 | Zubler | 219/635 |
| 2006/0261503 A1 | * | 11/2006 | Sago et al. | 264/16 |
| 2007/0057391 A1 | * | 3/2007 | Ibsen et al. | 264/16 |
| 2007/0292597 A1 | * | 12/2007 | Ritzberger et al. | 427/2.29 |
| 2008/0193900 A1 | * | 8/2008 | Veyrat | 433/223 |
| 2009/0239198 A1 | * | 9/2009 | Gritsch et al. | 433/202.1 |
| 2009/0239199 A1 | * | 9/2009 | Cadario et al. | 433/203.1 |

FOREIGN PATENT DOCUMENTS

| | | |
|---|---|---|
| DE | 10241857 | 4/2003 |
| EP | 0231773 | 8/1987 |
| GB | 514830 | 11/1939 |

* cited by examiner

*Primary Examiner*—Joseph S Del Sole
*Assistant Examiner*—Nahida Sultana
(74) *Attorney, Agent, or Firm*—Ann M. Knab

(57) ABSTRACT

The present invention relates to a method and a system for preparing dental restorations from ceramic or polymeric material to achieve color and opacity gradients simulating natural dentition, wherein an ingot of ceramic or polymeric material is entirely or partially forced through a system of channels in a press mold into a mold cavity in the press mold, wherein the mold cavity corresponds to a dental restoration.

26 Claims, 5 Drawing Sheets

SYSTEM FOR PREPARING DENTAL RESTORATIONS

REFERENCE TO RELATED APPLICATIONS

This application claims priority pursuant to 35 U.S.C. §119 to European Patent Application No. 07023059.4 filed Nov. 28, 2007.

BACKGROUND

The present invention relates to a method and a system for preparing dental restorations from ceramic or polymeric material to achieve color and opacity gradients that simulate natural dentition.

A molding method such as that described for example in EP 0 231 773 A1 or U.S. Pat. No. 5,702,514 A is known for the preparation of dental restorations from ceramic material. In that method, a model of a dental restoration made of a material that can be burned out completely is fitted onto a strand forming the later casting channel inside a press muffle and the press muffle is filled with an investment material, so that the model is completely surrounded by the investment material. The investment material is cured to form a refractory press mold and the model is burned out, in order to produce the mold cavity corresponding to a dental restoration in the cured press mold. A ceramic material is then forced through the casting channel into the press mold by applying pressure, in order to fill the mold cavity corresponding to the dental restoration and consequently produce the dental restoration from the ceramic material.

A disadvantage of the known methods and systems is that the known molding methods are only suitable for dental restorations of a single color. If a naturally appearing reproduction in the form of a dental restoration of color and opacity gradients that occur in a great variety of natural dentition is desired, then according to the prior art, a subsequent surface treatment, such as for example by painting or coating, is unavoidable. Such a subsequent surface treatment is laborious and expensive because of the manual work involved.

It is therefore an object of the present invention to provide a method and a system for preparing dental restorations from ceramic or polymeric material, wherein color and opacity gradients are achieved without subsequent surface coating.

SUMMARY OF THE INVENTION

These and other objects and advantages are accomplished by the method of preparing dental restorations from ceramic or polymeric materials to achieve color and opacity gradients that simulate natural dentition to provide a restoration having a natural appearance. In one aspect of the method of the invention, an ingot of ceramic or polymeric material is entirely or partially forced through a system of channels in a press mold into a mold cavity in the press mold, wherein the mold cavity corresponds to a dental restoration. The ingot has a first volume region and a second volume region wherein the second volume region differs from the first volume region by a different color or opacity, or by both color and opacity. The system of channels in the press mold directs the ingot into the mold cavity in the molding process in such a way that material of the first volume region reaches the mold cavity at an earlier time than material of the second volume region and/or more material of the first volume region than material of the second volume region is forced into the mold cavity.

According to a second aspect of the present invention, a system for preparing dental restorations from ceramic or polymeric material to achieve color and opacity gradients that simulate natural dentition is provided, wherein the system comprises an ingot of ceramic or plastic, a press muffle base and a sprue pin system of material that can be burned out completely. The sprue pin system fits onto the press muffle base and attaches to a model of a dental restoration. The sprue pin system and dental model are fabricated of material that can be burned out completely, so that a press mold with a system of channels corresponding to the sprue pin system and a mold cavity corresponding to the model can be produced by fitting the model onto the press muffle base via the sprue pin system. A press mold produced in this way is suitable for forcing an ingot into the mold cavity of the press mold. The ingot has a first volume region and a second volume region, the second volume region differing from the first volume region by a different color or opacity, or both color and opacity. The sprue pin system is prefabricated and configured in such a way that the system of channels created in the production of the press mold has two flow paths, the second flow path having a greater volume than the first flow path. The material of the first volume region is forced into the mold cavity through the first flow path and material of the second volume region is forced into the mold cavity through the second flow path in a molding process.

According to a third aspect of the present invention, use of an ingot fabricated of a ceramic or polymeric material for preparing dental restorations from ceramic or polymeric material to achieve colour and opacity gradients that simulate natural dentition is provided. The ingot has a first volume region and a second volume region wherein the second volume region differs from the first volume region by a different color or opacity. The ingot is entirely or partially forced through a system of channels in a press mold into a mold cavity in the press mold, wherein the mold cavity corresponds to a dental restoration. In the molding process, the system of channels in the press mold directs the ingot into the mold cavity in such a way that material of the first volume region reaches the mold cavity at an earlier time than material of the second mold region and/or more material of the first volume region than material of the second mold region is forced into the mold cavity.

In this description, the term "dental restoration" comprises crowns, partial crowns, veneers, bridges, abutments or other appliances. The present invention is also suitable for the overmolding of structures of ceramic, metal or metal alloys. The term "flow path" is defined as the path that the material of a volume region of the ingot follows in the molding process. The volume of a flow path is determined by the surface area of the material of a volume region along the flow path multiplied by the length of the flow path. According to the configuration of the system of channels, the flow path may, for example, divide and form branches that do not lead into the mold cavity. Flow paths of volume regions do not have to run through separate channels in the system of channels but may also run through a common channel. The total volume of a flow path is determined by the volume of the system of channels that is taken up by material of a volume region of the ingot after the molding process.

The invention also encompasses methods, systems and uses for the simultaneous or non-simultaneous preparation of any desired number of dental restorations with the same or different colour and opacity gradients involving the use of one or more systems of channels or sprue pin systems.

In a preferred embodiment of the method according to the invention, the system of channels and the mold cavity corresponding to a dental restoration are produced by a prefabricated sprue pin system made of material that can be burned out completely, such as acrylic or wax. Prior to the molding process, a model of a dental restoration made of material that can be burned out completely is fitted onto a press muffle base of a press muffle by means of the sprue pin system. The press muffle is then filled with a refractory die material or investment material so that the model and the sprue pin system are completely surrounded by the investment material. The investment material is cured to form a refractory press mold and the model and the sprue pin system are burned out, in order to produce the mold cavity corresponding to a dental restoration and the system of channels in the cured press mold.

Preferably, the model of a dental restoration is connected mesially or distally to the sprue pin system. This is more advantageous than attachment of sprue pins to an occlusal side of a restoration since the later detachment of the system of channels is easier and the geometry of the opposite teeth does not have to be taken into consideration.

In order to produce color and opacity gradients that simulate natural dentition in a dental restoration directly by the molding process, the ingot has, according to the invention, a first volume region and a second volume region, the second volume region differing from the first volume region by a different color or opacity or both color and opacity. The different volume regions may, for example, be a dentine material and an incisal material for the dental restoration. Often, a third volume region is also used, corresponding to a cervical dentine material. The number of volume regions is in principle unlimited.

Under the effect of pressure during the molding process of forcing the ingot, with optionally prior or simultaneous heating of the ingot, the material of the ingot, i.e. the ceramic or the polymer, becomes viscous or flowable and can be forced into a mold cavity in the press mold that corresponds to a dental restoration. Incidentally, the system of channels in the press mold directs the molding into the mold cavity in the molding process.

According to the method of the present invention, the ingot, which is flowable in the molding process, is directed into a mold cavity corresponding to a dental restoration in such a way that the first volume region of the molding reaches the mold cavity at a time before the second volume region. As a result, color and opacity gradients that simulate natural dentition are achieved in the dental restoration without the need for subsequent laborious coating and color characterization. Both the nominal volume fraction and the spatial position of the individual volume regions in the dental restoration are in this way controlled by the system of channels. The dental restoration exhibits a natural appearance as a result of the distribution of the differently colored or transparent volume regions of the ingot that is controlled by the system of channels.

In an aspect of the method according to the invention, the ingot of ceramic or polymeric material can be referred to as a press blank, which may be of a one-piece or multi-part form. In the case of a multi-part molding, the individual parts are fused together by heating or pressing together before the actual molding operation. Preferably, in this case each individual part represents a volume region with a specific color and/or opacity.

Preferably, the color or opacity gradient between the volume regions of the ingot is steady and gradual, which corresponds to the color variations in natural dentition. The ingot preferably has a molding direction, along which the cross-sectional area of the ingot is constant, so that the ingot can be forced into the press mold along the molding direction. The form of the molding may, in particular, be substantially cylindrical, although other shapes are possible including, but not limited to, round, rectangular, square or polygonal.

There are various possible ways in which the volume regions with different color or opacity gradients are distributed in the ingot. For example, the volume regions may extend substantially along the molding direction and be substantially adjacent to one another at a plane with a normal that extends substantially perpendicularly to the molding direction of the ingot. As an alternative to this, the volume regions may in each case substantially make up a layer of the ingot and be substantially adjacent to one another at a plane with a normal that extends substantially parallel to the molding direction of the ingot. In addition, it is also possible that the volume regions in each case make up a piece of the ingot and are substantially adjacent to one another at a plane with a normal that extends obliquely to the molding direction of the molding.

The ingot may have more than a first volume region and a second volume region, with additional volume regions differing neighbouring volume regions by a different colour or opacity.

In accordance with the configuration of the ingot with the at least two volume regions with a different color and/or opacity, the system of channels in the present mold must be configured such that it is adapted to the ingot. This is advantageously ensured by a prefabricated sprue pin system that matches a specific ingot. The system of channels must ensure that one volume region of the ingot reaches the mold cavity at a time before the other volume region. This can be achieved, for example, by a system of channels that has two flow paths, the second flow path having a greater volume than the first flow path, and the first volume region being forced into the mold cavity through the first flow path and the second volume region being forced into the mold cavity through the second flow path in the molding process. The flow paths may, for example, be separate channels, but they are not limited to separate channels. Both flow paths may lead through a common channel, the system of channels ensuring that one volume region of the ingot fills a greater volume of the system of channels than the other volume region in the molding process. Since uniform pressure prevails within the entire system of channels in the molding process, that is, along both flow paths, that volume region that fills a greater volume in the system of channels reaches the mold cavity later than that volume region that fills a smaller volume in the system of channels. The difference in the volume in the flow paths may be achieved, for example, by the sprue pin system being configured with an extension of the form of any shape that adds volume to the flow path or paths, so that a reservoir corresponding to the extension is obtained as part of the second flow path in the production of the press mold. As a result, during the molding process a reservoir is first filled with one volume region, so that this volume region reaches the mold cavity at a later time than the other volume region.

The configuration in the form of an extension also has the advantage that the volume of the extension, and consequently the resultant reservoir, can be reduced by shortening the extension before the press mold is produced. The sprue pin system can in this way be adapted to the desired color or opacity gradients in the dental restoration It may be preferable to provide an ingot that does not have an exact rotational symmetry along the molding direction. For example, if the volume regions do not make up disc-shaped regions of the ingot, the volume regions are arranged in the ingot in such a way that no rotational symmetry is obtained. With a disturbed rotational symmetry, a distinct orientation of the ingot in a plane with a normal that extends substantially parallel to the molding direction of the ingot is obtained within the press mold. Before the molding process, the ingot is located in a pressing space within the press mold, the pressing space being created by an extension of the press muffle base in the production of the press mold. Consequently, the form of the extension of the press muffle base should correspond substantially to the outer form of the ingot. To this extent, a disturbed rotational symmetry of the ingot is only advisable if the extension of the press muffle base has a corresponding disturbed rotational symmetry. This ensures that a distinct orientation of the ingot is achieved when it is inserted into the press space for the molding process before the production of the press mold by way of arranging the sprue pin system at the extension of the press muffle base.

For multi-part ingots, which may be put together as desired by the user to form an ingot for the molding process, it may also be advisable if the height of the extension of the press muffle base is adjustable, so that a press space with a corresponding depth is obtained in the press mold in the production of the press mold as a result of the adjusted height of the extension. The ingot is consequently not restricted to a specific height.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
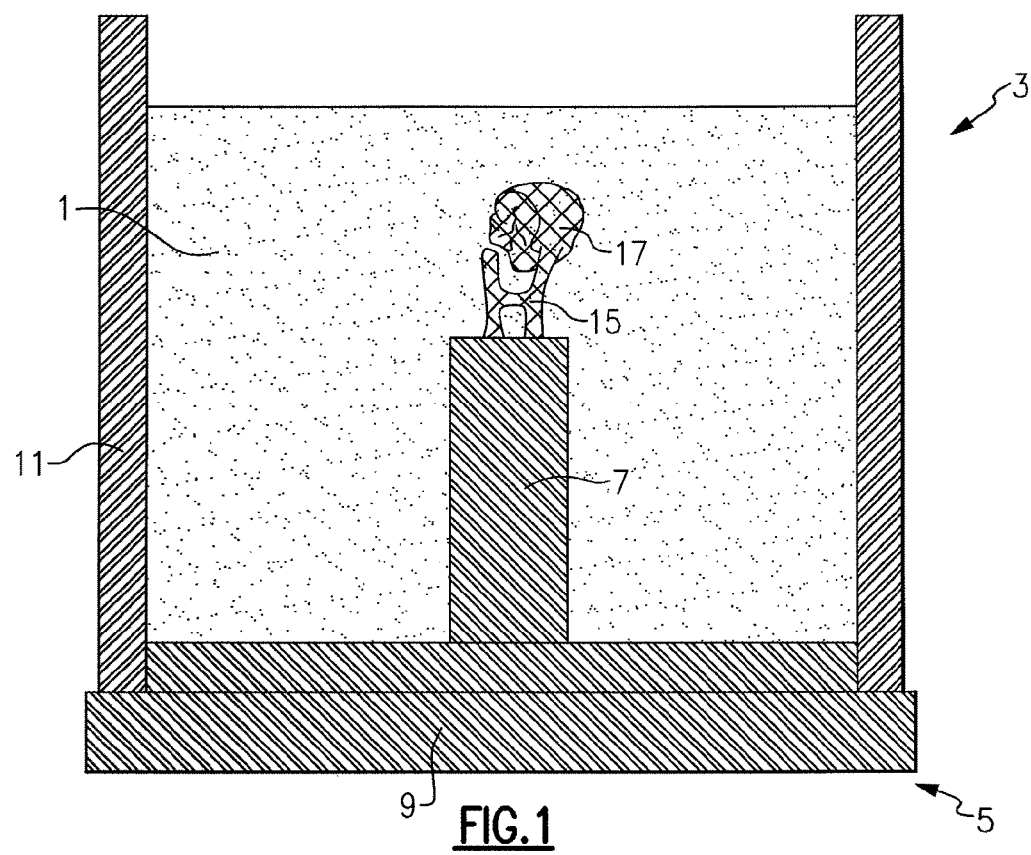
FIG. 1 is a schematic representation of a first preferred embodiment of the method or system according to the invention during the production of the press mold with a sprue pin system and a model of a dental restoration.

As will be appreciated, the present invention provides an effective and efficient method for manufacturing colored or shaded ceramic dental restorations. Reference is made to FIG. 1, which shows how a press mold 1 is produced by means of a press muffle 3 with a press muffle base 5. The press muffle base 5 includes a cylindrical extension 7, which extends upward from the plate-shaped bottom 9 of the press muffle base 5. A press muffle sleeve 11 fits flush with and onto the bottom 9, and consequently forms together with the bottom 9 an outer filling mold.

A sprue pin system 15, which is made of a material that can be burned out completely, such as for example plexiglass or wax, is placed on the upper end face of the cylindrical extension 7. In this embodiment, the sprue pin system 15 is H-shaped, being placed upright with both legs of the H-shape on the extension 7. Sprue pin system 15 may be any shape suitable to hold a model of a dental restoration. A model 17 of a dental restoration, likewise made of material that can be burned out completely, such as for example plexiglass or wax, is formed or fitted on one leg of the H-shape of pin system 15. The press muffle 3 is filled with an embedding compound or a refractory die material, which completely surrounds the extension 7, the sprue pin system 15 and the model 17. The embedding compound is any refractory die material, such as, but not limited to a gypsum-like, phosphate-bonded composition, comprising for example silica powder, and is initially flowable and cures to form the press mold 1 after filling in press mold 1. After curing, the "burn-out" process proceeds to burn out the material of sprue pin system 15 and model 17. The burn-out process leaves no residue from the sprue pin system 15 and of the model 17. Thereafter, the press muffle 3, including press muffle base 5, bottom 9 and extension 7, and press muffle sleeve 11 are detached from the press mold 1.

Figure 2:
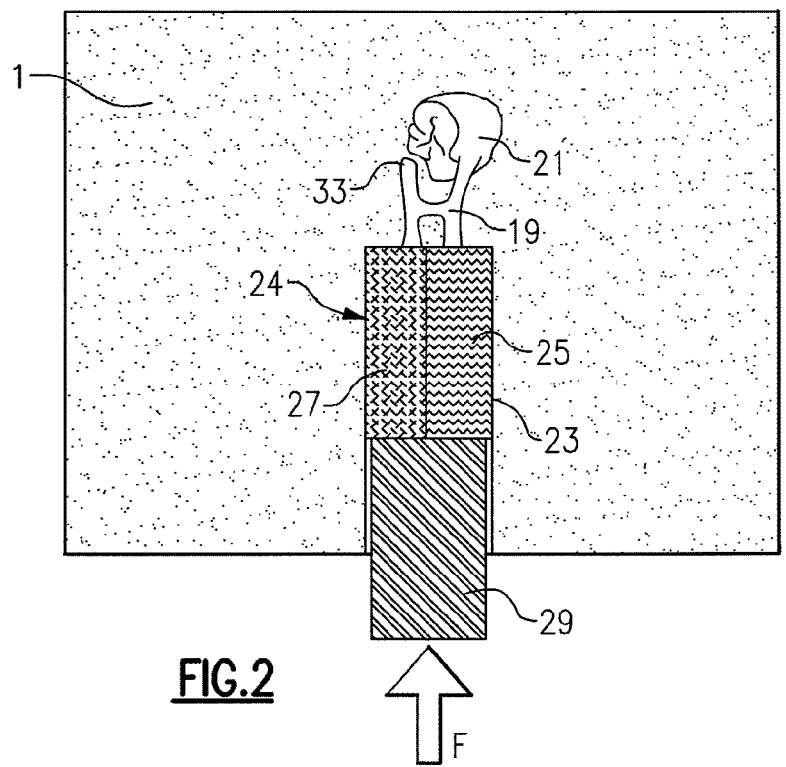
FIG. 2 is a schematic representation of a first preferred embodiment of the method or system according to the invention after the production of the press mold with a system of channels, a mold cavity and an ingot inserted into the press space of the press mold, before the molding operation.

FIG. 2 shows the press mold 1 after completion of the burn out process. The burned-out sprue pin system 15 creates a system of channels 19 and the burned-out model 17 creates a mold cavity 21 corresponding to the dental restoration model 17. The removed press muffle base 5, in combination with the extension 7 that extends into press mold 1, creates a press space 23 in the press mold 1.

An ingot 24, also known as a blank or pellet, is inserted in the press space 23. Ingot 24 has a first volume region 25 and a second volume region 27. The volume regions 25 and 27 differ from each other by their color and/or opacity. Although there appears to be a sharp contrast in color, opacity and other properties between the first volume region 25 and the second volume region 27 as suggested in the representation, the volume regions 25, 27 have steady, gradual and smooth transitions in accordance with the color variations in natural teeth. The ingot 24 has the same outer cylindrical form as the extension 7 of the press muffle base 5, so that it can be inserted with an exact fit into the press space 23.

A press ram or piston 29 with the same cylindrical form as press space 23 can then force the ingot 24 through the system of channels 19 into the mold cavity 21 as soon as the ingot 24 has become viscous or flowable under the effect of heat and/or pressure. In this embodiment, the two volume regions 25, 27 are in each case a half-cylinder of the ingot 24, which are adjacent to each other at an interface which has a normal that extends perpendicularly to the ingot direction, which is indicated by the force arrow F. The ingot 24 is oriented such that, before the molding process, an end face of the first volume region 25 is arranged directly in front of the leg of the H-shaped system of channels 19 into the mold cavity 21 that is directly adjoined by the mold cavity 21. The other leg of the H-shaped system of channels 19 has in the upper part a blind channel 33, which is not directly connected to the mold cavity 21 but only via the cross-channel and the upper part of the other leg. Before the molding process, the second volume region 27 is located with an end face directly in front of the leg with the blind channel 33, so that the second volume region 27 can only reach the mold cavity 21 via the cross-channel and the upper part of the other leg. Since the molding direction, as indicated by the force arrow F, runs in the longitudinal direction of the leg of the H-shaped system of channels 19, during the molding process, the blind channel 33 is filled with the second volume region 27 before the pressure forces the second volume region 27 laterally through the cross-channel and finally through the upper part of the leg that is directly connected to the mold cavity 21 into the mold cavity 21. Since the flow path of the second volume region 27 in the system of channels 19 has a greater volume than the flow path of the first volume region 25 in the system of channels 19, the first volume region 25 reaches the mold cavity 21 before the second volume region 27. As a result, a greater volume fraction of the mold cavity 21 is filled by the first volume region 25 then by the second volume region 27.

Figures 3A, 3B, 3C:
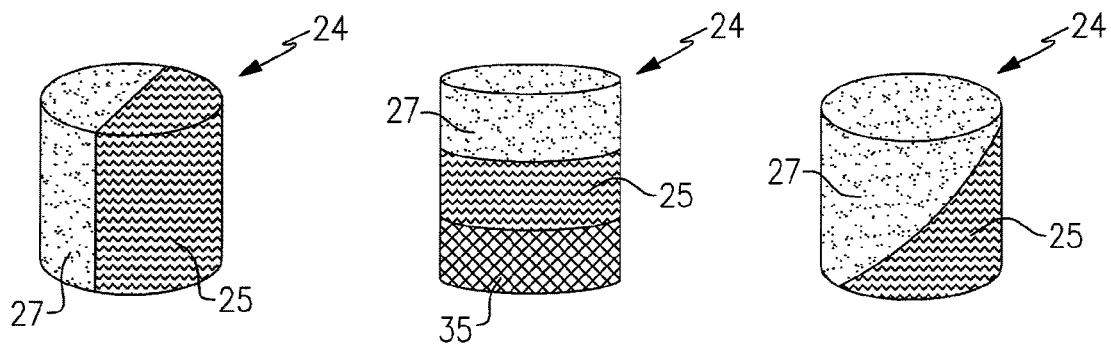
FIGS. 3a through 3c show embodiments of the ingot produced from the method or system according to the invention.

In FIG. 3, possible configurations of the ingot 24 are shown. Even if only cylindrical forms of the ingot 24 are shown, any other form that has a constant cross-sectional form along a molding direction is also conceivable. The volume regions 25, 27 may be distributed in the ingot 24 in various ways. In FIG. 3a, a distribution of the volume regions 25, 27 as half-cylinders is shown, corresponding to the exemplary embodiment from FIG. 2. FIG. 3b shows the individual volume regions 25, 27 as discs, axially aligned atop one another. Apart from the volume regions 25, 27, the ingot 24 may have an additional volume region 35 or a number of additional volume regions. With the distribution of the volume regions 25, 27, 35 as discs, a configuration of the system of channels 19 such as in FIG. 2 is unsuitable, and a system of channels 19 or a sprue pin system 15 with a configuration as shown in FIGS. 6, 7, 8 and 10 would have to be used. However, it is advantageous that the configuration of the volume regions as discs is conducive to providing the ingot 24 in a multi-part form. Individual parts in disc form then advantageously each form a volume region. The arrangement of the individual parts can then be put together as desired by the user. Before the actual molding operation, the individual parts are fused together under the effect of heat and/or pressure to form an ingot 24 with the corresponding volume regions. FIG. 3c shows that an interface between the volume regions 25 and 27 that is oriented obliquely in relation to the molding direction is also conceivable.

Figures 4A, 4C:
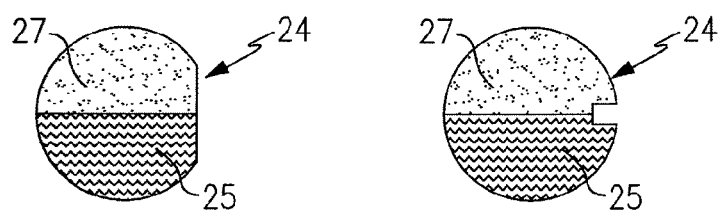
FIGS. 4a through 4d show embodiments of the ingot in the extension of the press muffle base of the method or system according to the invention for the distinct orientation of the ingot in the press mold.
Figures 4B, 4D:
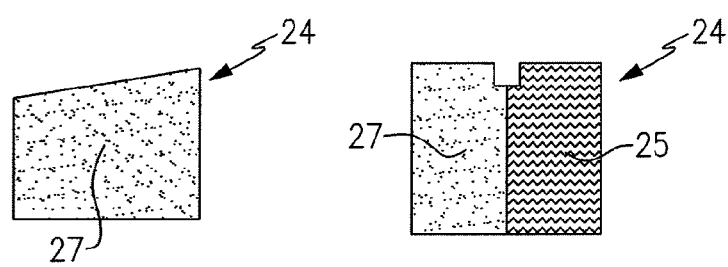

For the configurations of the ingot 24 according to FIGS. 3a and 3c or any other configuration in which the individual volume regions do not have the form of a disc, the orientation about the molding direction of the ingot 24 is not distinct. If, however, the configuration of the system of channels 19 requires a specific orientation about the molding direction of the ingot 24, as represented in the embodiment in FIG. 2, it is advisable to ensure a distinct orientation by the form of the ingot 24. FIGS. 4a through 4d show various possible ways in which the rotational symmetry of the ingot 24 about the molding direction can be disturbed in order that the orientation of the ingot 24 in the press space 23 of the press mold 1 is distinct. In this case, a distinct orientation is only ensured when the extension 7 of the press muffle base 5 has an analogous disturbance of the rotational symmetry. The end face of the ingot 24 that is to be introduced first into the press space 23 of the press mold 1 could, for example, be bevelled as shown in FIG. 4a, the gradient of the bevelling running along the borderline between the volume regions on the end face. The ingot 24 may also be flattened on one side of the lateral surface as shown in FIG. 4b, or have a groove or notch as shown in FIG. 4c. The end face that is to be introduced first into the press space 23 of the press mold may also have a notch or groove, as shown in FIG. 4d, to prevent rotational symmetrical ambiguity in the orientation about the molding direction. In any case, the press space 23 of the press mold 1 must have a corresponding shape or notch that creates a disturbance of the rotational symmetry, in order that the ingot 24 can be inserted with an exact fit and is then directly located in front of the system of channels 19 before the molding process. If parts of the sprue pin system 15 are configured in such a way that the system of channels 19 produced as a result makes up part of the press space 23 of the press mold 1 (see FIGS. 6, 7, 8 and 10), the sprue pin system 15 may also provide a corresponding disturbance of the rotational symmetry in the press space 23 of the press mold 1.

Figure 5A:
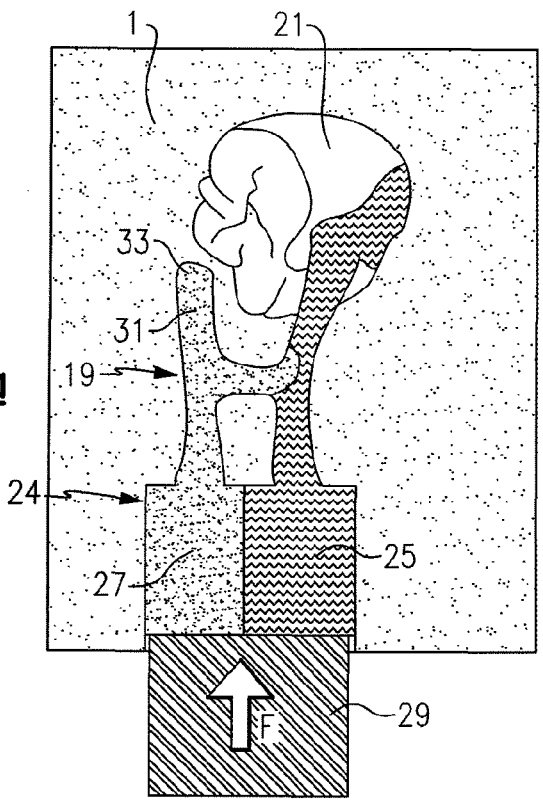
FIGS. 5a through 5b show a detailed representation of a first preferred embodiment of the method or system according to the invention during the molding operation.
Figure 5B:
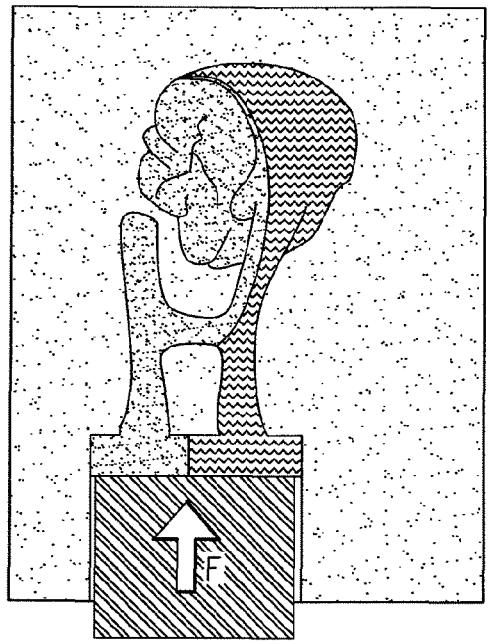

In FIGS. 5a and 5b, the embodiment according to FIG. 2 is shown in more detail during and after the molding process. While the first volume region 25 is already being forced into the mold cavity 21, the second volume region 27 is still on its way to the mold cavity 21 along the second flow path via the leg with the blind channel 33, the cross-channel and the upper part of the leg that is connected to the mold cavity 21. When this happens, the blind channel 33 is filled, since the pressure in the molding direction has first forced a first flow direction of the second volume region 27 into the blind channel 33 until the latter is filled. Once the blind channel 33 is filled, the flow direction of the second volume region 27 follows the cross-channel and finally the pressure in the molding direction forces it to the mold cavity 21 along the upper part of the leg that is connected to the mold cavity 21. The flow path that the flow direction of the second volume region 27 follows therefore has a greater volume than the flow path followed by the flow direction of the first volume region 25 to the mold cavity 21 directly through the leg that is connected to the mold cavity 21. In the upper part of the leg that is connected to the mold cavity 21, the volume regions 25, 27 are reunited.

After the molding process, the mold cavity 21 has a higher volume fraction of the first volume region 25 than of the second volume region 27. Color and opacity gradients creating natural tooth color and opacity effects are thereby achieved in the dental restoration. Following the molding process, the ingot 24, which has been forced into mold space 21, is cured. The press mold 1 is then removed by cutting, milling, sand-blasting, etching and/or other customary methods. Subsequently, the dental restoration, which comprises the filling of the mold cavity 21, is separated from the material of the ingot 24 that has filled the system of channels 19. At the point at which the model 17 was fitted on the sprue pin system 15, the dental restoration must be manually reworked in order to ensure mesial and distal surfaces of the dental restoration that correspond to the natural tooth. It is beneficial if the sprue pins for the model are not provided occlusally, but mesially or distally, since then the form of the opposite teeth does not have to be taken into consideration in the manual reworking.

Figure 6:
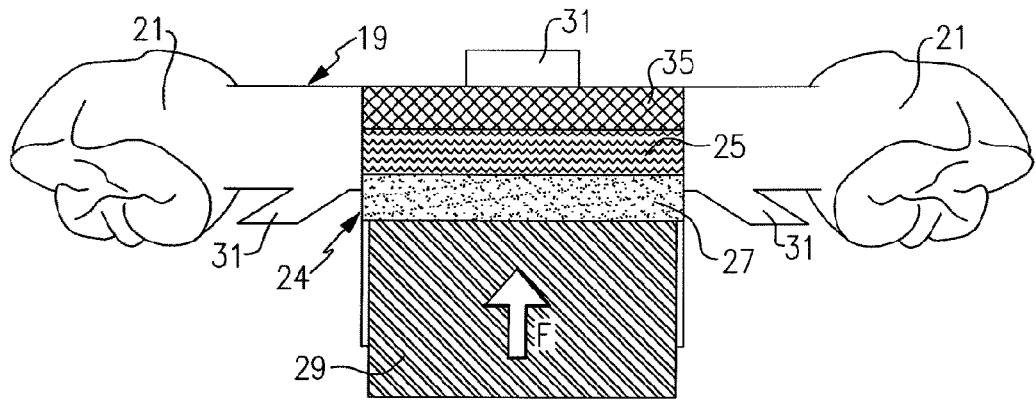
FIG. 6 is a detailed representation of a second preferred embodiment of the method or system according to the invention before the molding operation.
Figure 7:
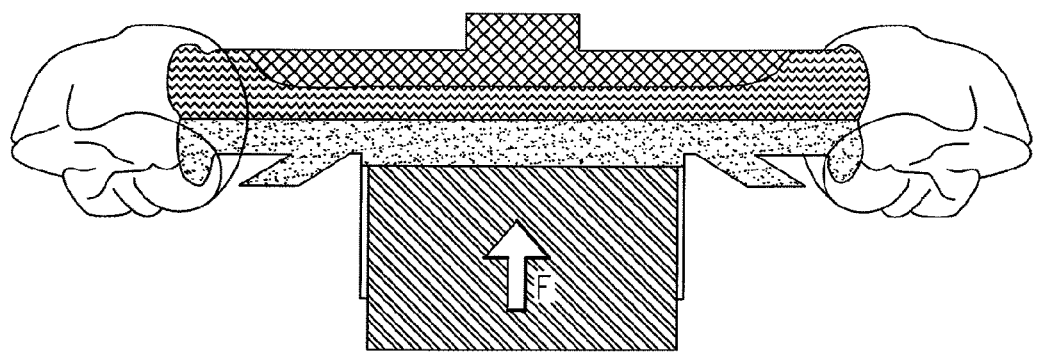
FIG. 7 is a detailed representation of a second preferred embodiment of the method or system according to the invention during the molding operation.
Figure 8:
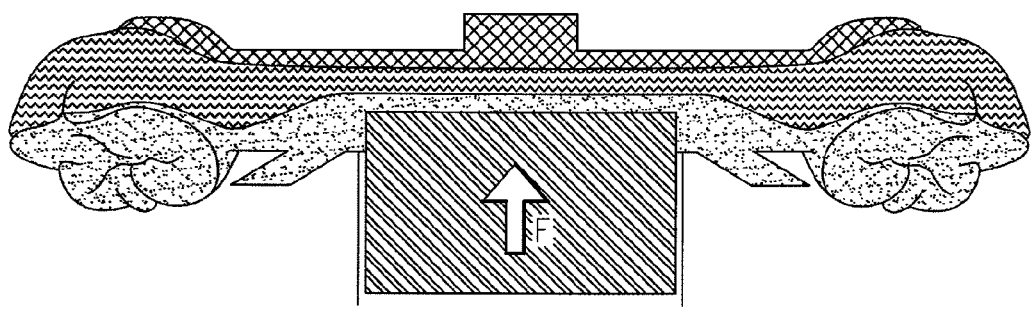
FIG. 8 is a detailed representation of a second preferred embodiment of the method or system according to the invention after the molding operation.

A further embodiment of the invention is shown in FIGS. 6, 7 and 8. This embodiment is particularly well suited for the simultaneous preparation of a number of dental restorations at the same time. This example encompasses two dental restorations that are prepared at the same time in one molding operation, but it may also encompass three or more restorations. In this example, an ingot 24, such as that shown in FIG. 3b, is used. The volume regions 25, 27 and 35 are in the form of discs and together form the cylindrical ingot 24. The volume region 25 corresponds to the dentine material, the volume region 27 corresponds to the incisal material and the volume region 35 corresponds to the cervical dentine material.

The system of channels 19 in the press mold 1 has been created by a sprue pin system 15 such as that shown in FIG. 10. The sprue pin system 15 substantially comprises a sheet of, for example, plastic or wax material and can be inserted into a continuous slit providing an exact fit on the end face of the extension 7 of the press muffle base 5. When this happens, the sprue pin system 15 completely fills the slit and protrudes laterally from the lateral surfaces of the extension 7 of the press muffle base 5. The models of the dental restorations are fitted onto these lateral protrusions. The sprue pin system 15 also has an extension 30, which protrudes from the end face of the extension 7 in the press muffle base 5 in the molding direction. In order that, after insertion, the sprue pin system 15 is also seated centrally in the slit on the end face of the extension 7 of the press muffle base 5, the sprue pin system 15 may have a tongue 39, which engages in a corresponding groove 41 in the slit on the end face of the extension 7 of the press muffle base 5. After the embedding, curing and burning out of the press mold 1, a system of channels 19 and two mold cavities 21 are obtained, as shown in FIGS. 6 to 8.

A third volume region 35 of the ingot 24 lies directly at the front edge of the press space 23 and a reservoir 31, which is obtained from the burned-out sprue pin system 15 with the extension 30. Further reservoirs 31 are arranged on the underside of the system of channels 19, in order that the flow path for the second volume region 27, i.e. the incisal material, runs through the volume of the lower reservoir 31. The number and configuration of reservoirs 31 and their arrangement and orientation on the system of channels 19 may be chosen as desired by way of the configuration of the sprue pin system 15.

The first volume region 25, here in the form of the dentine material, represents the middle layer, which is adjoined by the third volume region 35, that is to say the cervical dentine material, which is in direct contact with the press ram 29. FIG. 7 shows what happens when the ingot 24 is forced into channels 19. The third volume region 35 is forced into the reservoir 31 and also laterally into the channels, while the other volume regions 25, 27 are forced exclusively laterally into the channels. Since the lateral pressure during the filling of the upper reservoir 31 increases as it becomes more distant from the upper reservoir 31, the third volume region 35 experiences a lower lateral pressure than the other volume regions 25, 27, as long as the upper reservoir 31 is not yet filled. Only after the upper reservoir 31 is filled, the third volume region 35 is forced into the mold cavities 21 with the same force as the other volume regions 25, 27. The filling of the lower reservoir 31 with the second volume region 27, i.e. the incisal material, proceeds in an analogous way. As a result, less incisal material than dentine material is forced into the mold cavities 21.

As shown in FIG. 7, the third volume region 35 already lags behind the other volume regions 25, 27, so that less volume of the mold cavities 21 is filled by the third volume region 35, i.e. the cervical dentine material, than by the first volume region 25, i.e. the dentine material. Because of the reservoirs 31, a number of flow fronts or directions are obtained for the second volume region 27 and for the third volume region, partially extending into the reservoirs 31 and consequently forming in each case an overall flow path with a greater volume than the flow path of the first volume region 25.

Figure 9:
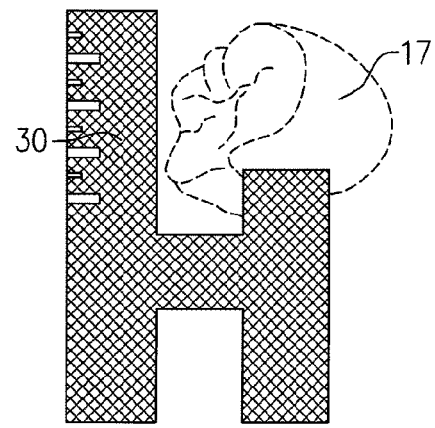
FIG. 9 shows an embodiment of the sprue pin system for producing a system of channels of the method or system according to the invention.
Figure 10A:
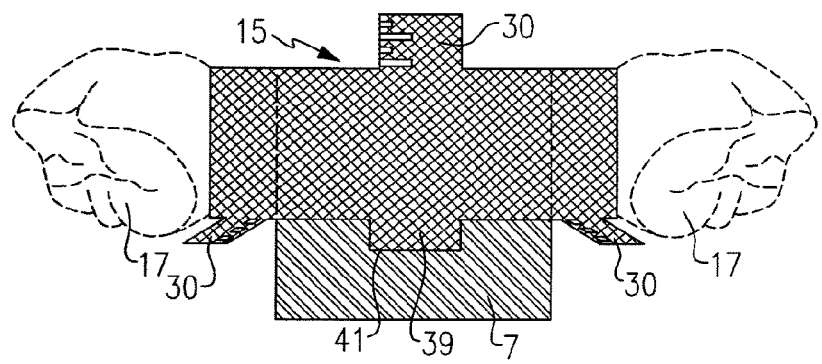
FIGS. 10a through 10d show further embodiments of the sprue pin system for producing a system of channels of the method or system according to the invention in connection with matching extensions of the press muffle base.
Figure 10B:
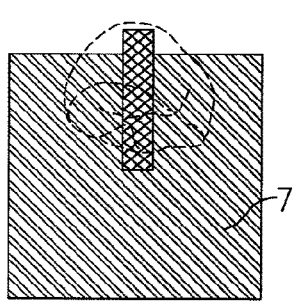
Figure 10C:
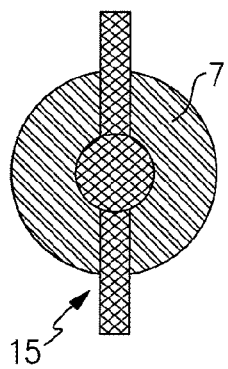
Figure 10D:
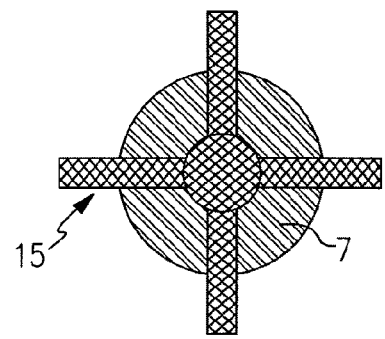

In FIG. 9, an H-shaped sprue pin system 15 corresponding to the first embodiment of FIG. 2 is represented. The leg of the H-shaped sprue pin system 15 that is not intended to provide a sprue pin for the model 17 has in the upper part an extension 30, which leads to a blind channel 33 in the creation of the press mold 1. Since the length of the extension 30 has an effect on the volume of the blind channel 33, and consequently directly on the volume fraction of the second volume region 27 in the dental restoration, it is advisable that the length of extension 30 be adjustable for the user. Consequently, the extension 30 advantageously has a scale, on the basis of which the user can shorten the length of the extension 30 by cutting it off, in order to achieve a desired distribution of the volume regions 25, 27 in the dental restoration. As shown in FIG. 10a, the extensions 30 of the second exemplary embodiment may also each have a scale for cutting off.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A system for preparing dental restorations from a ceramic or polymeric material to achieve colour and opacity gradients simulating natural dentition, wherein the system comprises:
    a mold cavity connected to a system of channels having a first flow path and a second flow path, wherein the second flow path has a greater volume than the first flow path;
    an ingot fabricated of a ceramic or polymeric material;
    a press muffle and a press muffle base that form a press mold;
    wherein the press muffle base has an extension that has a shape that corresponds to the shape of the ingot, wherein the extension forms a press space in the press mold;
    wherein the ingot comprises a first volume region and a second volume region, wherein the first and second volume regions differ in color or opacity or both color and opacity;
    wherein the first volume region is forced into the first flow path and the second volume region is forced into the second flow path such that the first volume region fills in a first portion of the mold cavity and the second volume region fills in a second portion of the mold cavity.

2. The system of claim 1 wherein the system of channels comprises additional flow paths and wherein the ingot comprises additional volume regions for flowing into the additional flow paths.

3. The system of claim 2 wherein the additional volume regions of the ingot have different color or opacity or different color and opacity.

4. The system of claim 3 wherein the mold cavity and system of channels are located in a press mold.

5. The system of claim 1 wherein the mold cavity and system of channels are formed from a model and attached sprue pin system, whereby the model and attached sprue system are fabricated of a material that can be burned out completely.

6. The system of claim 2 wherein the first, second and additional volume regions are separate components that are fused together by pressing and/or heating to form the ingot.

7. The system of claim 5 wherein the sprue pin system comprises an extension that forms a reservoir in the system of channels, whereby the extension comprises a scale marking various lengths on the extension for shortening the extension.

8. The system of claim 2 wherein the first, second and/or additional flow paths comprise a reservoir to increase the volume of the flow path.

9. The system of claim 1 further comprising additional mold cavities connected to the system of channels.

10. The system of claim 2 wherein the color and/or opacity of the first, second and additional volume regions is consistent throughout each region.

11. The system of claim 2 wherein the ingot is cylindrical, round, rectangular, square or polygonal in shape.

12. The system of claim 1 wherein the first volume region and the second volume region extend substantially along the same molding direction and are substantially adjacent to one another at a plane with a normal that is substantially parallel to the molding direction.

13. The system of claim 1 wherein the first volume region and the second volume region extend substantially along the same molding direction and are substantially adjacent to one another at a plane with a normal that extends obliquely to the molding direction.

14. The system of claim 1 wherein the first volume region and the second volume region are axially aligned one atop of the other.

15. The system of claim 2 wherein the first volume region, the second volume region, and additional volume regions are axially aligned one atop of the other.

16. The system of claim 1 wherein the first volume region is greater in volume than the second volume region.

17. The system of claim 1 wherein the ingot comprises an anti-rotational component for proper orientation of the ingot in the press mold.

18. The system of claim 17 wherein the anti-rotational component comprises a groove, bevel, or flattened section on the ingot.

19. The system of claim 1 wherein a height of the extension is adjustable.

20. The system of claim 5 wherein the material that can be burned out completely comprises acrylic or wax.

21. The system of claim 5 wherein the sprue pin system is configured with an extension, whereby the extension produces a reservoir in the second flow path in the production of the system of channels, wherein the height and volume of the extension can be adjusted to produce a reservoir of desired height and volume.

22. The system of claim 5 wherein the sprue pin system is configured to connect to two or more models of dental restorations.

23. The system of claim 1 further comprising a piston, wherein the piston is configured to fit within the press space and forces the ingot through the system of channels.

24. The system of claim 1 wherein the first volume region and the second volume region comprise a full volume region or a partial volume region.

25. The system of claim 2 wherein the additional volume regions comprise a full volume region or a partial volume region.

26. A system for preparing dental restorations from a ceramic or polymeric material to achieve colour and opacity gradients simulating natural dentition, wherein the system comprises:
- a mold cavity connected to a system of channels having a first flow path and a second flow path, wherein the second flow path has a greater volume than the first flow path;
- an ingot fabricated of a ceramic or polymeric material;
- wherein the ingot comprises a first volume region and a second volume region, wherein the first and second volume regions differ in color or opacity or both color and opacity;
- wherein the first volume region is forced into the first flow path and the second volume region is forced into the second flow path such that the first volume region fills in a first portion of the mold cavity and the second volume region fills in a second portion of the mold cavity;
- wherein the mold cavity and system of channels are formed from a model and attached sprue pin system, whereby the model and attached sprue system are fabricated of a material that can be burned out completely.

* * * * *